United States Patent [19]
Daniell et al.

[11] Patent Number: 6,050,260
[45] Date of Patent: Apr. 18, 2000

[54] HUMIDIFIER SLEEP APNEA TREATMENT APPARATUS

[75] Inventors: Michael Grenfell Daniell; Lewis George Gradon, both of Auckland, New Zealand

[73] Assignee: Fisher & Paykel Limited, Auckland, New Zealand

[21] Appl. No.: 08/982,069

[22] Filed: Dec. 1, 1997

[30] Foreign Application Priority Data

Dec. 2, 1996 [NZ] New Zealand ............................ 299857
Apr. 23, 1997 [NZ] New Zealand ............................ 314659

[51] Int. Cl.⁷ .................................................. A61M 16/00
[52] U.S. Cl. ................................. 128/204.22; 128/203.16; 128/203.12; 128/203.17; 128/204.14
[58] Field of Search ...................... 128/204.22, 204.14, 128/204.13, 204.17, 205.11, 203.12, 203.17, 203.16, 202.22, 202.27, 204.21, 203.27, 206.29, 203.25

[56] References Cited

U.S. PATENT DOCUMENTS

| | | | |
|---|---|---|---|
| 4,378,795 | 4/1983 | Feathers et al. | 128/202.27 |
| 4,381,267 | 4/1983 | Jackson | 128/204.13 |
| 4,674,492 | 6/1987 | Niemeyer et al. | 128/202.22 |
| 4,821,709 | 4/1989 | Jensen et al. | 128/205.11 |
| 4,941,469 | 7/1990 | Adahan | 128/205.11 |
| 5,031,612 | 7/1991 | Clementi | 128/204.14 |
| 5,065,756 | 11/1991 | Rapoport | 128/205.25 |
| 5,117,819 | 6/1992 | Servidio et al. | 128/204.21 |
| 5,146,915 | 9/1992 | Montgomery | 128/203.27 |
| 5,349,946 | 9/1994 | McComb | 128/203.17 |
| 5,368,786 | 11/1994 | Dinauer et al. | 128/203.12 |
| 5,452,714 | 9/1995 | Anderson et al. | 128/205.11 |
| 5,537,997 | 7/1996 | Mechlenburg et al. | 128/204.21 |
| 5,626,128 | 5/1997 | Bradley et al. | 128/206.29 |

FOREIGN PATENT DOCUMENTS

4105971 8/1992 Germany ........................ 128/203.25

*Primary Examiner*—John G. Weiss
*Assistant Examiner*—V. Srivastava
*Attorney, Agent, or Firm*—Trexler, Bushnell, Giangiorgi & Blackstone, Ltd.

[57] ABSTRACT

Apparatus and method of treating OSA (Obstructve Sleep Apnea) are disclosed wherein a Positive Airway Pressure device is utilized to provide a gases supply which is then passed through a humidifier. As the amount of water vapor generated by the humidifier is very low at start up (typically the humidifier comprises a water container on a heating plate) the pressure of gases supplied by the apparatus are controlled so that the humidity of the gases supplied to a patient are always at the maximum of the capability of the humidifier to humidify that air flow.

27 Claims, 6 Drawing Sheets

HUMIDIFIER SLEEP APNEA TREATMENT APPARATUS

BACKGROUND OF THE INVENTION

1. Field of the Invention

This invention relates to healthcare apparatus and in paroular, though not solely to humidified Positive Airway Pressure (PAP) apparatus used in the treatment of Obstructive Sleep Apnea (OSA) and a method of controlling such apparatus.

2. Description of the Prior Art

OSA is a sleep disorder which affects up to at least 5% of the population in which muscles which normally hold the airway open relax and ultimately collapse, sealing the airway. The sleep pattern of an OSA sufferer is characterised by repeated sequences of snoring, breathing difficulty, lack of breathing, waking with a start and then returning to sleep. Often the sufferer is unaware of this pattern occurring. Sufferers of OSA usually experience daytime drowsiness and irritability due to a lack of good continuous sleep.

In an effort to treat OSA sufferers, a technique known as Continuous Positive Airway Pressure (CPAP) was devised, A CPAP device consists of a gases supply (or blower) with a conduit connected to supply pressurised gases to apatient, usually through a nasal mask. The pressurised air supplied to the patient effectively assists the muscles to keep the patient's airway open, eliminating the typical OSA sleep pattern.

The use of a CPAP system is known to have side effects such as dehydration of the airways and nasal passages which may lead to Rhinitis (inflammation of the nasal passages). The side effects mean that the patient is less likely to comply with his or her CPAP therapy and the therapy itself may cause an increase in meal resistance as a response to the high air flow, degrading the pressure level applied to the airway and thereby reducing the effectiveness of the therapy. Accordingly, a humidified CPAP system would be an improvement. An improvement on the standard CPAP system is described in U.S. Pat. No. 5,537,997 assigned to Respironics Inc. in which a humidifier is incorporated with the CPAP system so that the patient receives humidified gases.

However, a mere combination of a well known humidifier (in which gases are passed through water vapour rising from the surface of water in a water humidification chamber on top of a heaterplate) and a CPAP device would not maximise the benefit of the humidified CPAP therapy to the patient. This is due to the heater plate talig some time to warm up so that the patient would, on some occasions, bc supplied with gases which were not humidified. It should be noted that the sensitive tissues of the nasal passage can be caused to swell after receiving only as little as 10 minutes of non-humidified gases flow. Accordingly, it would be an advantage if the gases received by the patient were always humidified to the capability of the humidifier at any point in time.

Currently, CPAP treatment is delivered via nasal mask. Some patients find a nasal mask claustrophobic and arc therefore unlikely to tolerate the treatment Some OSA sufferers are obligate mouth breathers and unable to tolerate nasal application of gases. A smaller orally attached mouthpiece or mask would be more readily accepted by most patients. In addition, the resistance to gases flow through the nasal passageway is much greater than the resistance to gases flow through the mouth Therefore, the pressure and flow rates of supplied gases could be lowered for orally applied positive airway pressure systems which further means that the breathing attachment could be made lighter and easier to wear.

However, in order to orally deliver gases to a patient, it is very important that the gases are sufficiently humidified at all times. If not, parts of the mouth can dry out within very short times (for example 10 seconds) causing discomfort. In other parts of the mouth salivary glands canbecorne over stimulated causing excess saliva, swallowing difficulties and further discomfort.

It is therefore an object of the present invention to provide breathing assistance apparatus which will at least go some way towards overcoming the above disadvantages or which will at least provide the public with a useful choice.

Accordingly, in a first aspect, the invention consists in breathing assistance apparatus adapted to deliver gases to a patient to assist said patient's breathing comprising:

gases supply means, including pressure regulating means adapted to supply gases at a required pressure level, gases pressure sensing means to determine the pressure of said supplied gases, humidification means which receive said supplied gases and humidify said gases, said humidification means capable of variably humidifying said gases up to a reed humidity level, humidified gases transportation pathway means which channel said humidified gases to said patient, gases humidity sensing means to determine the humidity of the gases supplied to said patient, control means which in response to gases humidity and pressure information supplied by said gases pressure and gases humidity sensing moans, controls the pressure of gases supplied by said gases supply means so that the gases flow passing through said humidification means is limited to an amount which can be humidified to said required humidity level by the humidification means at its present humidity level.

In a second aspect, the invention consists in a method of operating breathing assistance apparatus, said breathing assistance apparatus comprising gases supply means, gases pressure regulating means, gases humidification means, humidified gases transportation means and control means storing predetermined required pressure and humidity indication values programmed to carry out the steps of:

i) initiating said gases humidification means to humidify the gases from said gases supply means, ii) sensing the pressure of said gases, iii) sensing the humidity of said gases, iv) deter g a difference pressure value between said predetermined required pressure value and said sensed pressure value, v) determining a difference humidity value between said predetermined required humidity value and said sensed humidity value, vi) calculating a required average rate of increase of pressure with respect to humidity by dividing said difference pressure value by said difference humidity value, and vii) controlling said gases pressure regulating means to increase the pressure of said gases at said required average rate of increase until said predetermined required pressure value is attained.

In a third aspect the invention consists in a method of treating breathing disorders in a patient comprising tie steps of:

i) generating a gases flow, ii) humidifying said gases flow iii) supplying said gases flow to said patient via said patient's mouth.

BRIEF DESCRIPTION OF THE DRAWINGS

The invention consists in the foregoing and also envisages constructions of which the following gives examples.

One preferred form of the present invention will now be described with reference to the accompanying drawings in which.

DETAILED DESCRIPTION OF THE PREFERRED EMBODIMENT

Figure 1:
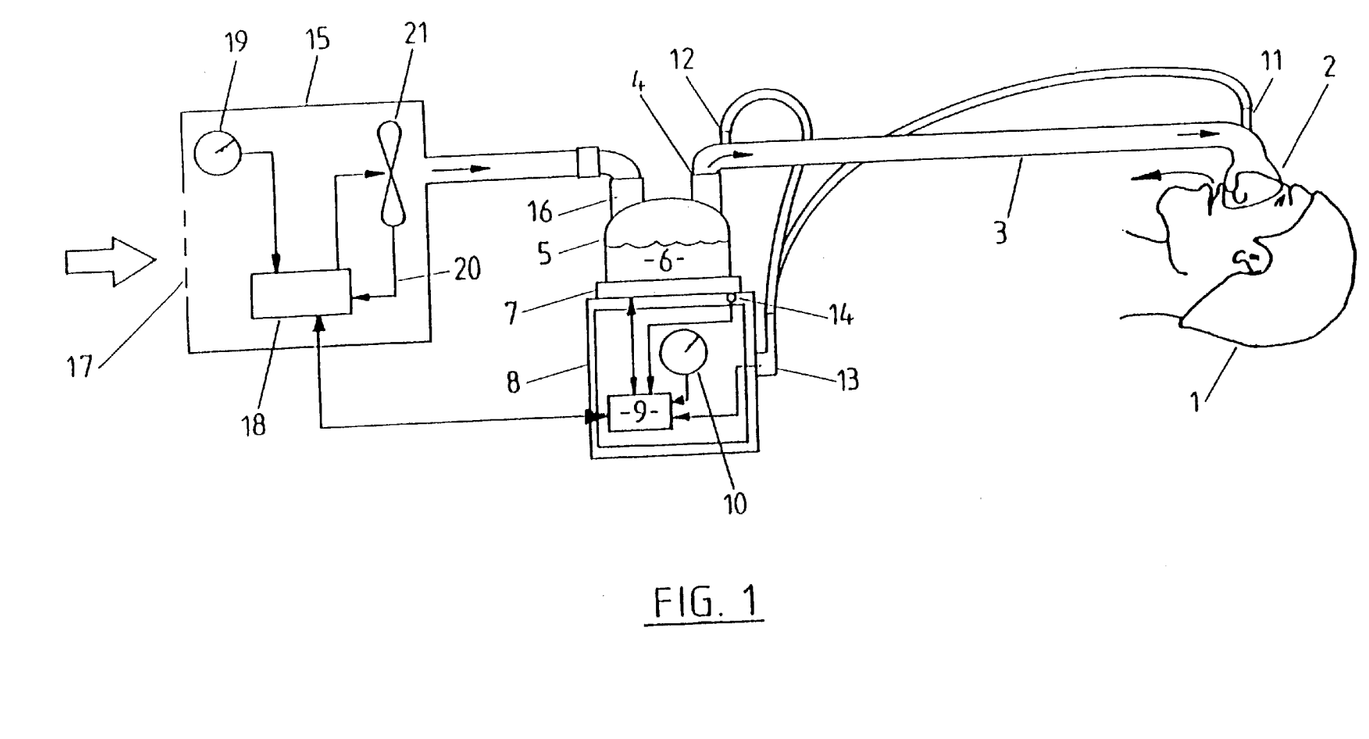
FIG. 1 is a block diagram of a humidified Continuous Positive Airway Pressure (CPAP) system in accordance with a preferred embodiment of the present invention.

With reference to FIG. 1 a humidified Continuous Positive Airway Pressure (CPAP) system is shown in which a patient 1 is receiving humidified and pressurised gases through a nasal mask 2 connected to a humidified gases transportation pathway or inspiratory conduit 3. It should be understood that the present invention, however, is not limited to the delivery of CPAP gases but is also applicable to other types of gases delivery systems such as VPAP (Variable Positive Airway Pressure) and BiPAP (Bi-level Positive Airway Pressure). Inspiratory conduit 3 is connected to the outlet 4 of a humidification chamber 5 which contains a volume of water 6. Inspiratory conduit 3 may contain heating means or heater wires (not shown) which heat the walls of the conduit to reduce condensation of humidified gases within the conduit. Humidification chamber 6 is preferably formed from a plastics material and may have a highly heat conductive base (for example an aluminium base) which is in direct contact with a heater plate 7 of humidifier 8. Humidifier 8 is provided with control means or electronic controller 9 which may comprise a microprocessor based controller executing computer software commands stored in associated memory.

Controller 9 receives input from sources such as user input means or dial 10 through which a user of the device may, for example, set a predetermined required value (preset value) of humidity or temperature of the gases supplied to patient 1. The controller may also receive input from other sources, for example temperature and/or flow velocity sensors 11 and 12 through connector 13 and heater plate temperature sensor 14. In response to the user set humidity or temperature value input via dial 10 and the other inputs, controller 9 determines when (or to what level) to energise heater plate 7 to heat the water 6 within humidification chamber 5. As the volume of water 6 within humidification chamber 5 is heated, water vapour begins to fill the volume of the chamber above the water's surface and is passed out of the humidification chamber 5 outlet 4 with the flow of gases (for example air) provided from a gases supply means or blower 15 which enters the chamber through inlet 16. It should be noted that it is possible to obtain the relationship between the humidity of the gases in humidification chamber 5 and the temperature of the heater plate 7. Accordingly, it is possible to utilise the heater plate temperature in an algorithm or a look-up table to determine the humidity of the gases (accordingly, the heater plate temperature acts as an indication of the humidity of the gases and the two terms are used interchangeably in this specification). Exhaled gases from the patient's mouth are passed directly to ambient surroundings in FIG. 1. It should also be noted that in the preferred form of the present invention, heater plate temperature is utilised to represent humidity, however, any suitable humidity sensor could alternatively be used.

Blower 15 is provided with variable pressure regulating means or variable speed fan 21 which draws air or other gases through blower inlet 17. The speed of variable speed fan 21 is controlled by after control mean or electronic controller 18 (or alternatively the function of controller 18 could carried out by controller 9) in response to inputs from controller 9 and a user set predetermined required value (preset value) of pressure or fan speed (as has been mentioned above in relation to heater plate temperature and humidity, it is also possible to determine a relationship between fan speed and gases pressure and the two terms are therefore used interchangeably in this specification) via dial 19.

In use, a user of the humidified CPAP system determines a required "set" (or required) value of gases pressure ($P_{set}$) to be delivered by blower 15 to the patient 1. This set value is entered to controller 18 by dial 19. The user also determines a required "set" (or required) value of temperature ($T_{set}$ for the heater plate 7 which is entered to controller 9 via dial 10. The set temperature user input dial may be labelled "Humidity" for the user's convenience. Controller 9 then determines the present temperature of heater plate 7 ($T_{actual}$) through sensor 14 and the present gases pressure ($P_{actual}$) for example, from speed sensor 20. It should be noted that it could take up to 30 minutes for the gases to reach their set humidity level, depending upon ambient conditions, flow rates and any obstructions in the patient's airway (for example inflammation). The present pressure value may be determined by a pressure or flow sensor within blower 15, humidification chamber 5 or the conduits connecting the system or, alternatively, as has already been mentioned the speed of fan 21 (sensed by speed sensor 20 or alternatively the command speed issued to the fan by controller 18 may be utilised as the acul fan speed) may be used to represent the gases pressure.

Controller 9 then utilises the set and actual values of temperature (representing humidity) and pressure (or fan speed) to control the humidification and pressure of the gases flow to patient 1. The pressure and temperature (humidity) of the gases supplied to the patient will eventually be allowed to reach their values set by the user, however, to ensure that the patient is always supplied with humidified gases which have been saturated with the maximum possible amount of water vapour (within the limits of the humidifier), controller 9 controls the speed of fan 21 in step with the humidity of the gases (or in step with the temperature of the heater plate 7). As an example (with reference to FIGS. 3 and 4), the following table sets out the sensed (initial) and set (or required) temperature and (relative) pressure (equating to fan speed) values at start up of the system.

Figure 3:
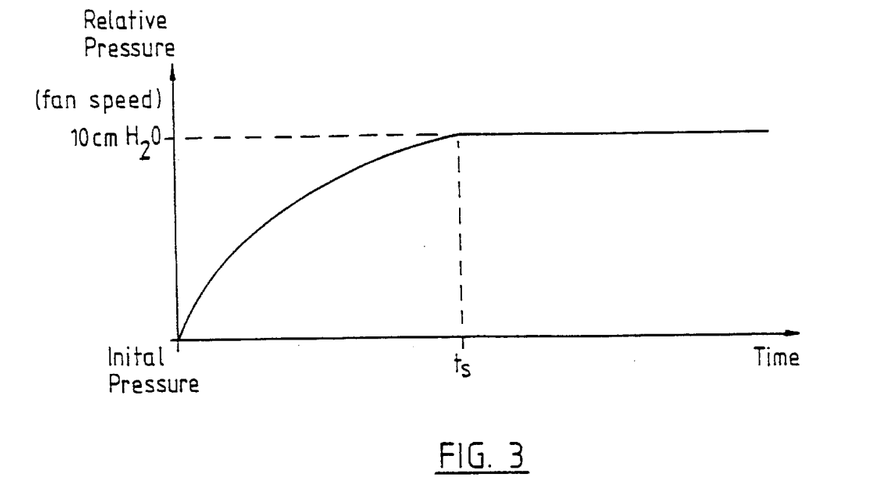
FIG. 3 is an example graph of air pressure (fan speed) versus time for the humidified CPAP system according to the present invention.
Figure 4:
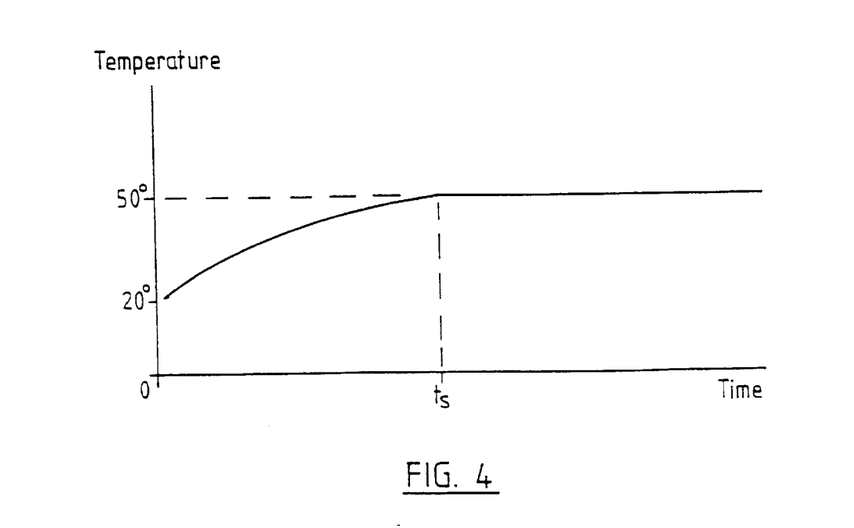
FIG. 4 is an example (corresponding to FIG. 3) graph of humidity (actually heater plate temperature) versus time for the humidified CPAP system according to the present invention.

|  | Temperature | Pressure |
|---|---|---|
| Initial | 20° C. | 0 cmH$_2$O |
| Set | 50° C. | 10 cmH$_2$O |

Controller 9 then determines the required change in pressure ($\Delta P$) and the required change in temperature ($\Delta T$) to obtained the required set pressure and temperature respectively of the system. In the present case:

| $\Delta P$ = 10 cm H$_2$O | $\Delta T$ = 30° C. |
|---|---|

Controller 9 then determines the required average rate of increase of pressure with respect to temperature by dividing $\Delta P$ by $\Delta T$. In the present case this calculation equates to 10 cmH$_2$O/30° C. or ⅓ cmH$_2$O per ° C.

Accordingly, for each 1° C. increase in heater plate 7 temperature, controller 9 will instruct controller 18 to increase the speed of fin 21 to achieve ⅓ cmH$_2$O increase in pressure in this example. In this way, both the temperature and pressure of the gases supplied to the patient will reach their set values at the same time (that is at time t$_s$ in FIGS. 3 and 4). Preferably the heater plate will be energised upon initiation of the humidified CPAP system and will gradually increase in temperature up to its set temperature (as shown in FIG. 4) at which time controller 9 will continuously suitably de-energise the heater plate and then re-energise the heater plate to maintain the set temperature. It should be noted that controller 9 could either continually monitor the heater plate temperature until the set temperature is reached and continually determine updated required average rate of increase values or the initially determined required average rate of increase could be used through the entire warm-up period. In tis way the patient will only ever receive humidified gases because at startup, what little water vapour is present in humidification chamber 5 will be carried by a light gases flow while when the heater plate reaches its required set value (and therefore much more water vapour is being generated in the humidification chamber) the blower will be controlled to generate a larger volume flow rate of gases.

In cases where the heater plate temperature is near the set temperature at start up of the system (for example when the patient has been using the device but has been called away temporarily and switched the device off or placed the device into a standby mode), the controller may do away with keeping the temperate and pressure in step as they increase. In this case, the controller first determines whether the actual heater plate temperature is about or greater than about 75% of its required set value. If this is the case then the speed of fan 21 is controlled to increase from zero to the required set value over a predetermined period of time (for example 15 minutes). Alternatively, the controller could determine if the actual heater plate temperature is within a range, for example a range of about 10° C., of the required set temperature value and then control the speed of fan 21 to reach the set value of fan speed in a predetermined period of time. These alternative steps are required due to the fact that as the heater plate is already warm it will soon reach its set temperature (before the patient has fallen asleep) and therefore the full fan speed should be delayed for a set period to allow the gases to be humidified within the capability of the humidifier to humidify the gases and/or to allow the user to achieve sleep before maximum flow rate occurs. The predetermined period of time could be set by the manufacturer prior to sale of the device or alternatively this value could be user controllable by for example adding a firer dial and input to the controller 9.

Figure 2:
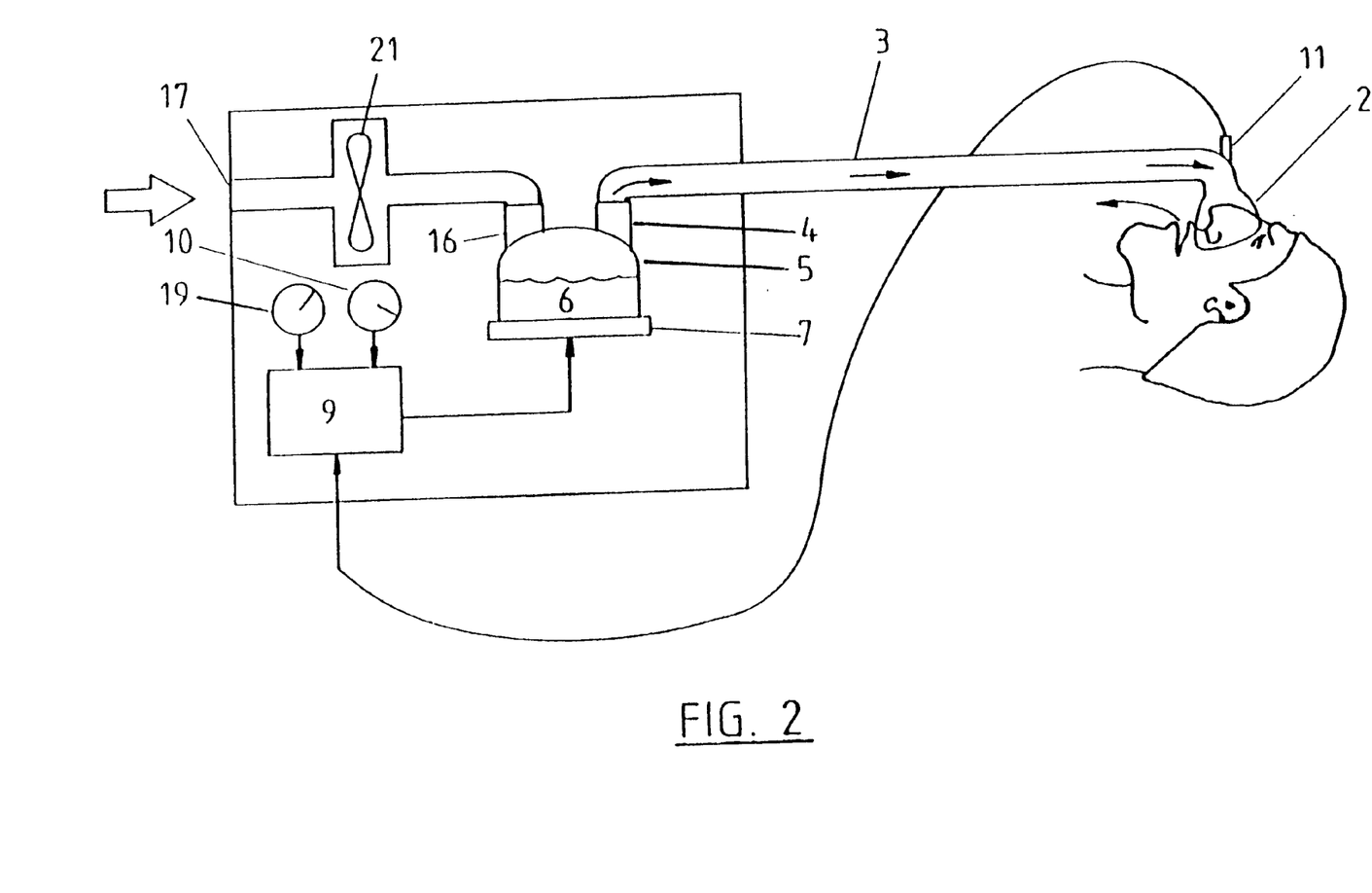
FIG. 2 is a block diagram of a humidified CPAP system in accordance with a further preferred embodiment of the present invention.

An alternative preferred embodiment of a humidified CPAP system is shown in FIG. 2 where the humidifier has been incorporated within blower 15 so that the system comprises only one main component connected to the patient via the same conduit 3 and nose mask 2. Only one controller 9 is required in this embodiment. All reference numerals common to FIG. 1 represent the same features of the invention.

Figure 5:
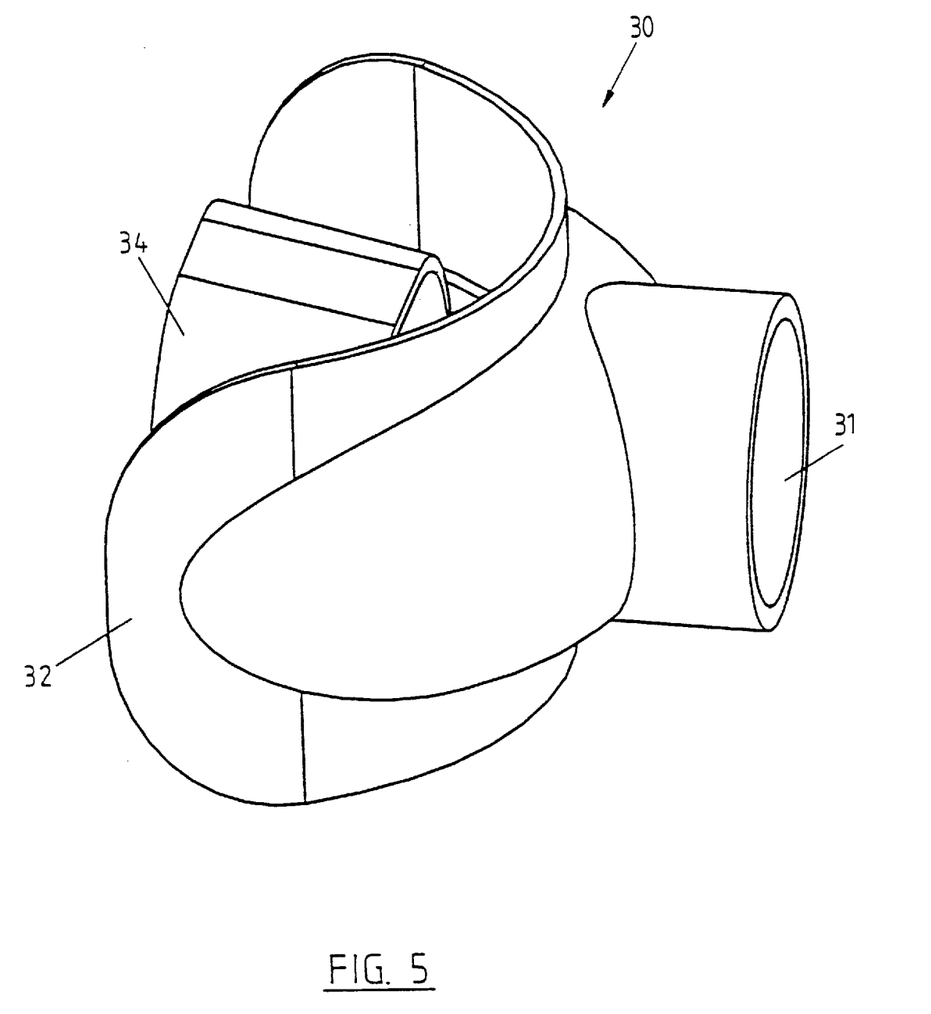
FIG. 5 is a side perspective view of a mouthpiece suitable for use with the system of FIG. 1 during oral administration of gases.
Figure 6:
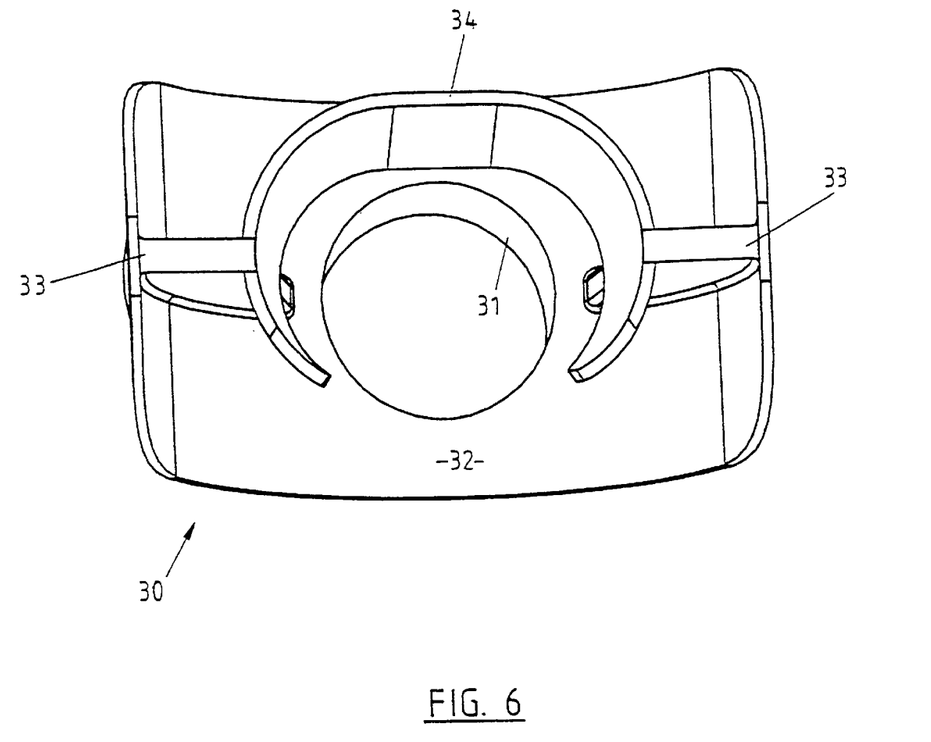
FIG. 6 is a rear view of the mouthpiece of FIG. 5.

As mentioned previously, it would be advantageous to deliver gases to a patient via the mouth. As the humidity and pressure control system described above ensures that the patient will be delivered with gases which are always adequately humidified respective of flow rate this is now possible. FIGS. 5 and 6 depict a suitable example mouthpiece 30 to be worn by the patient to allow humidity and pressure controlled gases to be orally delivered.

Mouthpiece 30 is similar in design to the mouthpiece of a diver's scuba equipment or snorkel mouth fitting with opening 31 to allow connection of inspiratory conduit 3 so that gases may be delivered to the patient's mouth. Lip separating means 32 are adapted to be worn by the patient (in the mouth) between the teeth and the lips. Lip separating means 32 are curved to match the curve of the teeth (horizontally from cheek to cheek) and extend vertically to near the join between the patient's lips and gums. Teeth separating means 33 are supplied on either side of mouthpiece 30 and adapted to be worn between the patient's teeth while an internal positioning means 34 is adapted to be positioned against the roof of the patient's mouth. It can therefore be seen that mouthpiece 30 will both be held in place, by virtue of the lip and teeth parting means (especially when "bitten down upon" by the patient and will also allow a free unobstructed passage trough the patient's lips and teeth for the humidity and pressure controlled gases.

Figure 7:
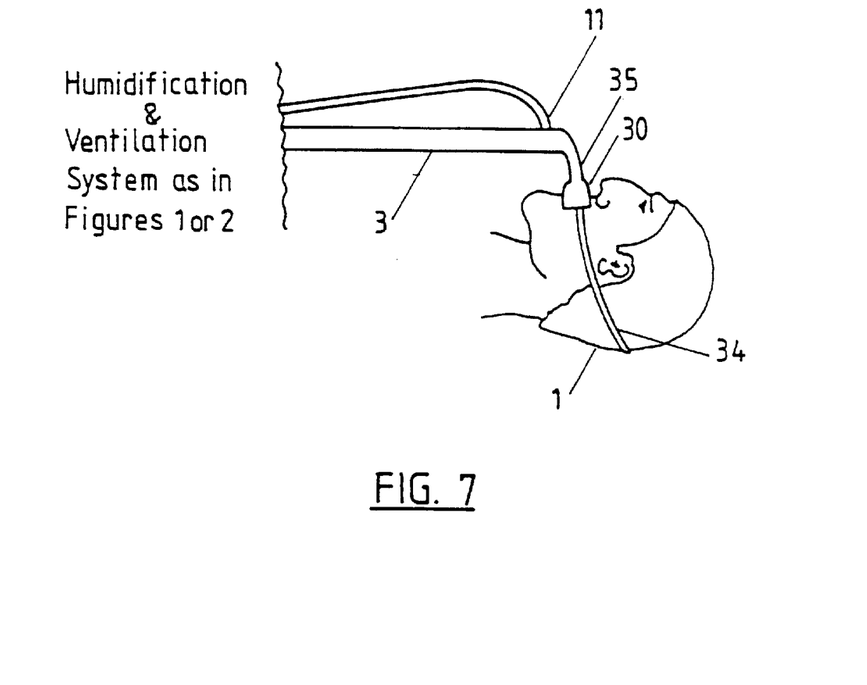
FIG. 7 is a partial schematic diagram of an orally delivered humidified CPAP system in accordance with a further embodiment of the present invention and, FIG. 8 is an enlarged cross-sectional view of the swivel fitting in FIG. 7.

A harness maybe fitted to mouthpiece 30 to assist in attaching it to the patient. For example, a strap 34 may be attached to either side of lip separating means 32 and passed around the patient's head. FIG. 7 shows the mouthpiece fitted to a patient who is receiving pressure and humidity controlled gases generated as described with reference to either one of FIGS. 1 or 2.

Figure 8:
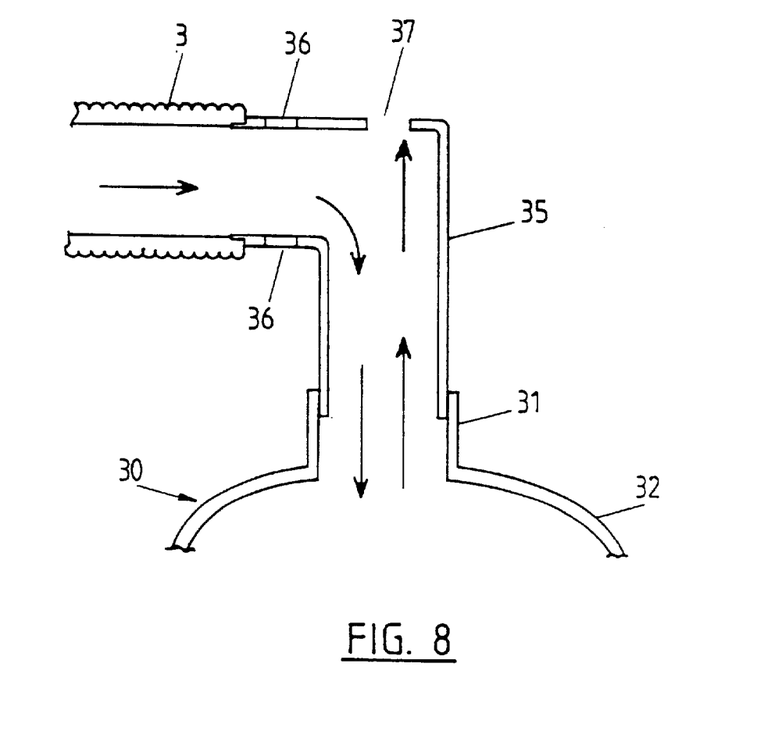

The patient may exhale through the nasal passage or through the mouth as desired If exhalation is through the mouth then a path for these gases must be provided. Accordingly, preferably a swivel fitting 35 is connected between the respiratory conduit 3 and the opening 31 of mouthpiece 30. FIG. 8 shows a swivel fitting 35 which includes a swivel and/or pivot section 36 and allows the patient to move during sleep without placing stress upon the conduit/mouthpiece connector Conduit 3 is thus allowed to pivot and/or swivel with respect to the mouthpiece 30. In addition swivel fitting 35 includes an outlet 37 through which the patient's exhilatory gases may pass (if exhalation is through the mouth) and also enables a constant pressure to be maintained at the entrance to mouthpiece 30. However, in some cases it is possible for some of the inhilatory gases to pass directly in through the patient's mouth and out of the patient through the nasal passage without being inhaled. This "leakage" causes a pressure drop in the inhilatory air flow at the patient's mouth detracting from the effect of the CPAP treatment. Accordingly, it may be desirable to provide suitable nasal passage blocking means (such as a nose clip or peg or plugs) as part of the apparatus to avoid this situation.

Accordingly, the present invention provides a humidified breathing assistance system in which the patient is provided with beneficially humidified gases during the period when the humidifier is warming up and also when the humidifier is running (and at its set temperature). In addition, the humidity of the gases supplied to the patient are maintained throughout both of these periods within the limits of the humidifiers ability to humidify those gases to the benefit of the patient making it possible to deliver gases orally to treat disorders such as Obstructive Sleep Apnea. This is extremely beneficial to the patient as even a flow of unhumidified gases or insufficiently humidified gases to the patient for a short duration of time (for example 10 minutes) cm cause detrimental swelling of the nasal passages and even greater discomfort if delivered orally.

We claim:

1. Breathing assistance apparatus for delivering gases to a patient to assist said patient's breathing comprising:

gases supply means, including pressure regulating means for supplying gases at a required pressure level, means for providing an indication of the actual pressure of said gases, humidification means which receive said supply gases and variably humidify said gases up to a required humidity level, humidified gases transportation pathway means which channel said humidified gases to said patient, means for providing an indication of the humidity of said gases, and control means programmed with stored instructions which in response to gases humidity and pressure information supplied by said means for providing an indication of the gases humidity and pressure, controls the pressure of gases supplied by said gases supply means so that the gases flow passing through said humidification means is limited to an amount which can be humidified to said required humidity level by said humidification means.

2. Breathing assistance apparatus as claimed in claim 1 wherein said breathing assistance apparatus is used in the treatment of Obstructve Sleep Apnea and also comprise mouthpiece means adapted to be worn by the patient in the region of the mouth, said mouthpiece means receiving said humidified gases supply from said humidified gases transportation pathway means.

3. Breathing assistance apparatus as claimed in claim 2 wherein said mouthpiece means includes gases outlet means to allow exhilatory gases from said patient to be expelled through said mouthpiece means to the ambient surroundings.

4. Breathing assistance apparatus as claimed in claim 1 or claim 2 also comprising nasal passage blocking means to prevent the inspiratory humidified gases from escaping directly through said patient's nasal passage.

5. Breathing assistance apparatus as claimed in claim 1 or claim 2 wherein said mouthpiece means is connected to said humidified gases transportation pathway means by swivel fitting means to allow relative pivotal movement therebetween while maintaining a sealed pathway for said gases flow.

6. Breathing assistance apparatus as claimed in claim 1 or claim 2 wherein said mouthpiece means comprise:

lip separating means which are adapted in use to ensure that said patient's lips are apart to allow said humidified gases to enter said patient's mouth, and teeth separating means adapted to be positioned between said patient's upper and lower sets of teeth over at least a part of said patient's teeth set, said lip separating means also providing a gripping surface so that said patient's lips when closed around said mouthpiece means, hold said mouthpiece means in said padent's mouth.

7. Breathing assistance apparatus as claimed in claim 1 or claim 2 wherein said control means controls the pressure of gases supplied by said gases supply means in step with changes in the humidity of said gases.

8. Breathing assistance apparatus as claimed in claim 1 or claim 2 wherein said control means determines a difference humidity value between said predetermined required humidity value and the value obtained from said means for providing an indication of the gases humidity, said control means also determines a difference pressure value between the predetermined required pressure value and the value obtained from said means for providing an indication of the gases pressure, a required average rate of increase of pressure with respect to humidity is then determined by dividing said difference pressure value by said difference humidity value and said control means controls said variable pressure regulating means to increase the pressure of said gases at said required average rate of increase until said predetermined required pressure value is attained.

9. Breathing assistance apparatus as claimed in claim 1 or claim 2 wherein said humidification means comprise a humidification chamber means adapted to receive a volume of water and a heating means to heat said water to produce water vapour within said chamber, said gases passing through said water vapour in said chamber and thereby being humidified.

10. Breathing assistance apparatus as claimed in claim 1 or claim 2 wherein said means for providing an indication of the pressure of said gases comprises a speed sensor which senses an indication of the speed of said gases passing through said humidified gases transportation pathway means.

11. Breathing assistance apparatus as claimed in claim 1 or claim 2 wherein said pressure regulating means comprise a variable speed fan and said means for providing an indication of the pressure of said gases comprises a speed sensor which senses the speed of said fan to provide said control means with said gases pressure information.

12. Breathing assistance apparatus as claimed in claim 1 or claim 2 wherein said means for providing an indication of the humidity of said gases comprise a temperature sensor sensing the temperature of said heating means to provide said control means with said gases humidity information.

13. Breathing assistance apparatus as claimed in claim 1 or claim 2 wherein said control means also controls said pressure regulating means to increase the pressure of said gases from zero to said predetermined required pressure value over a fixed period of time if the initial humidity value determined from said means for providing an indication of the humidity of said gases is at or greater than about 75% of said required humidity value.

14. Breathing assistance apparatus as claimed in claim 12 wherein said control means also controls said pressure regulating means to increase the presume of said gases from zero to said predetermined required pressure value over a fixed period of time if the initial humidity value determined from said means for providing an indication of the humidity of said gases is a predetermined difference below said required humidity value.

15. Breathing assistance apparatus as claimed in claim 14 wherein said predetermined difference relates to a temperature difference as sensed by said temperature sensor of approximately 10° C.

16. A method of operating breathing assistance apparatus comprising the steps of:
   i) providing a breathing assistance apparatus including gases supply means, gases pressure regulating means, gases humidification means, humidified gases transportation means and control means storing predetermined required pressure and humidity values,
   ii) initiating said gases humidification means to humidify the gases from said gases supply means,
   iii) sensing an indication of the pressure of said gases,
   iv) sensing an indication of the humidity of said gases,
   v) determining a difference pressure value between said predetermined required pressure value and said sensed indicative pressure value,
   vi) determining a difference humidity value between said predetermined required humidity value and said sensed indicative humidity value,
   vii) calculating a required average rate of increase of pressure with respect to humidity by dividing said difference pressure value by said difference humidity value, and
   viii) controlling said gases pressure regulating means to increase the pressure of said gases at said required average rate of increase until said predetermined required pressure value is attained.

17. A method of operating breathing assistance apparatus as claimed in claim 16 wherein said method is used in the treatment of Obstructive Sleep Apnea and also includes the step of supplying said gases to the mouth of a patient.

18. A method of operating breathing assistance apparatus as claimed in claim 16 or claim 17 wherein said step of controlling said gases pressure regulating means includes the step of
   ix) repeating steps (iii) to (viii) so that value of said required average rate of increase of pressure is continually updated in line with changes in the gases humidification means ability to humidify said gases.

19. A method of operating breathing assistance apparatus as claimed in claim 16 or claim 17 wherein subsequent to said step (iv) of sensing an indication of the humidity of said gases, said method also includes the step of
   iva) deciding if the initially sensed indicative value of the humidity of said gases is at or greater than about 75% of said predetermined required humidity value, in which case the following steps (v) to (viii) are omitted and said control means controls said gases supply means to increase the pressure of said gases from zero to said predetermined required pressure value over a fixed period of time.

20. A method of operating breathing assistance apparatus as claimed in claim 16 or claim 17 wherein subsequent to said step (iv) of sensing an indication of the humidity of said gases, said method also includes the step of
   iva) deciding if the initially sensed indicative value of the humidity of said gases is within a predetermined range of said required humidity value, in which case the following steps (v) to (viii) are omitted and said control means controls said gases supply means to increase the pressure of said gases from zero to said predetermined required pressure value over a fixed period of time.

21. A method of operating breathing assistance apparatus as claimed in claim 20 wherein said step of sensing an indication of the humidity of said gases is achieved by a temperature sensor sensing the temperature of said heating means to provide said control means with said gases humidity information wherein said predetermined range is about 10° C.

22. A method of treating Obstructive Sleep Apnea in a patient comprising the steps of:
   i) generating a gases flow,
   ii) humidifying said gases flow,
   iii) supplying said gases flow to said patient via said patient's mouth, and
   iv) automatically controlling the pressure of said gases flow in line with stored instructions so that said pressure increases in line with increases in the humidity of said gases flow.

23. A method of treating Obstructive Sleep Apnea in a patient comprising the steps of:
   i) generating a gases flow;
   ii) humidifying said gases flow,
   iii) supplying said gases flow to said patient via said patient's mouth,
   iv) sensing an indication of the pressure of said gases,
   v) sensing an indication of the humidity of said gases,
   vi) determining a difference pressure value between a predetermined required pressure value and said sensed indicative pressure value,
   vii) determining a difference humidity value between a predetermined required humidity value and said sensed indicative humidity value,
   viii) calculating a required average rate of increase of pressure with respect to humidity by dividing said difference pressure value by said difference humidity value, and
   ix) controlling the pressure of said gases at said required average rate of increase until said predetermined required value is attained.

24. A method of treating Obstructive Sleep Apnea in a patient as claimed in claim 23 wherein said step of controlling the pressure of said gases includes the step of repeating steps (iv) to (ix) so that said value of required average rate of increase of pressure is continually updated.

25. A method of treating Obstructive Sleep Apnea in a patient as claimed in clam 23 wherein subsequent to said step (v) of sensing an indication of the humidity of said gases, said method also includes the step of deciding if the initially sensed humidity of said gases is at or greater than about 75% of said predetermined required humidity value, in which case said control means controls said gases supply means to increase the pressure of said gases from zero to said predetermined required pressure value over a fixed period of time.

26. A method of treating Obstructive Sleep Apnea in a patient as claimed in claim 23 wherein subsequent to said step (v) of sensing an indication of the humidity of said gases, said method also includes the step of deciding if the initially sensed humidity of said gases is within a predetermined range of said required humidity value, in which case said control means controls said gases supply means to increase the pressure of said gases from zero to said predetermined required pressure value over a fixed period of time.

27. A method of treating Obstructive Sleep Apnea in a patient as claimed in claim 26 wherein said step of sensing an indication of the humidity of said gases is achieved by a temperature sensor sensing the temperature of said heating means to provide said control means with said gases humidity information wherein said predetermined range is about 10° C.

* * * * *

UNITED STATES PATENT AND TRADEMARK OFFICE
CERTIFICATE OF CORRECTION

PATENT NO. : 6,050,260
DATED : April 18, 2000
INVENTOR(S) : Michael Grenfell Daniell and Lewis George Gradon It is certified that error appears in the above-identified patent and that said Letters Patent is hereby corrected as shown below:

Column 1, Line 8 "paroular" should be -- particular --
Column 2, Line 51 "deter g" should be -- determining --
Column 2, Line 66 "tie" should be -- the --
Column 5, Line 45 "tis" should be -- this --
Column 6, Line 10 "firer dial" should be -- further dial --
Column 6, Line 10 "trough" should be -- through --
Column 7, Line 23 "cm cause" should be -- can cause --
Column 8, Line 15 "padent's '" should be -- patient's --

Signed and Sealed this

Twenty-seventh Day of March, 2001

Attest:

NICHOLAS P. GODICI

Attesting Officer

Acting Director of the United States Patent and Trademark Office